United States Patent

Alzani et al.

[11] Patent Number: 5,859,046
[45] Date of Patent: Jan. 12, 1999

[54] BIOLOGICALLY ACTIVE OREIDO DERIVATIVES USEFUL IN THE TREATMENT OF MULTIPLE SCLEROSIS

[75] Inventors: Rachele Alzani; Elena Cozzi; Nicola Mongelli; Andrea Lombardi Borgia; Massimo Temponi; Francesco Colotta, all of Milan, Italy

[73] Assignee: Pharmacia & Upjohn S.p.A., Milan, Italy

[21] Appl. No.: 930,598

[22] PCT Filed: Jan. 24, 1997

[86] PCT No.: PCT/EP97/00412

§ 371 Date: Oct. 9, 1997

§ 102(e) Date: Oct. 9, 1997

[87] PCT Pub. No.: WO97/28796

PCT Pub. Date: Aug. 14, 1997

[30] Foreign Application Priority Data

Feb. 9, 1996 [GB] United Kingdom .................... 9602721

[51] Int. Cl.$^6$ .................................................. A61K 31/395
[52] U.S. Cl. ............................................................ 514/422
[58] Field of Search ................................................. 514/422

[56] References Cited

U.S. PATENT DOCUMENTS 5,534,539 7/1996 Mongelli et al. ...................... 514/422

FOREIGN PATENT DOCUMENTS 94-23718 10/1994 WIPO .................................... 514/422

Primary Examiner—James H. Reamer
Attorney, Agent, or Firm—Oblon, Spivak, McClelland, Maier & Neustadt, P.C.

[57] ABSTRACT

Use, in the preparation of a medicament for use in the treatment of multiple sclerosis, of a compound which is a ureido derivative of formula (I)

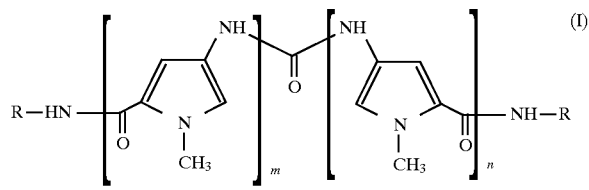

wherein each of m and n, which are the same, is an integer of 1 to 3; and each of the R groups, which are the same, is a naphthyl group substituted by 1 to 3 sulfonic acid groups, or a pharmaceutically acceptable salt thereof.

9 Claims, 2 Drawing Sheets

Fig. 1

Fig. 2

BIOLOGICALLY ACTIVE OREIDO DERIVATIVES USEFUL IN THE TREATMENT OF MULTIPLE SCLEROSIS

FIELD OF THE INVENTION

The present invention relates to the use of ureido derivatives of substituted pyrroles in the treatment of multiple sclerosis in mammals, including humans.

DESCRIPTION OF THE BACKGROUND

Multiple sclerosis is a demyelinating disease of the central nervous system the onset of which generally occurs within the age range from about 15 to 45. Myelin is a fatty substance which forms a sheath around certain nerve fibers and which conducts nervous impulse at a rate which enables muscles to make precise and delicate movements. The disease is characterized by induration of the sheath substance leading to the formation of plaques of varying size and location which interfere with the impulses normally conducted by the sheath.

The course of the disease can be highly variable in individual patients. Early stages of the disease in general are characterized by relapsing and remitting phase, subsequently the disease follows a chronic progressive course. However, the disease generally results in progressive deterioration of the control of muscle function with ultimate paralysis in many cases. The precise cause of multiple sclerosis is unknown and it may result from a complex interaction of a number of different factors.

Accordingly, there is a need in therapy for drugs which are active in treating the acute relapse and the progression of multiple sclerosis and/or able to ameliorate clinical symptoms or causes of multiple sclerosis.

PCT/EP94/00268 and PCT/EP94/00984 describe the use of a selected class of poly-4-amino-2-carbonyl-1-methyl pyrrole compounds, which were disclosed in PCT/EP91/00014, in preventing and/or treating the metastatic spread of tumors and the use in the treatment of lentivirus infection, respectively.

SUMMARY OF THE INVENTION

The present invention provides the use of a compound which is a ureido derivative of formula (I)

wherein each of m and n, which are the same, is an integer of 1 to 3; and each of the R groups, which are the same, is a naphthyl group substituted by 1 to 3 sulfonic groups, or a pharmaceutically acceptable salt thereof; in the manufacture of a medicament for use in the treatment of multiple sclerosis.

Accordingly, the present invention provides a use as defined above, wherein the medicament is for use in treating relapse, in particular acute relapse, and the progression of multiple sclerosis and in ameliorating clinical symptoms and causes of multiple sclerosis.

The present invention also provides a method of treating a mammal, including a human subject, suffering from multiple sclerosis which comprises administering to the said mammal an effective amount of a compound as defined above.

DETAILED DESCRIPTION OF THE INVENTION

The substituted naphthyl group is preferably a 5-, 6-, 7- or 8-naphthyl group, typically a 7- or 8-naphthyl group. When the naphthyl group is substituted by three sulfonic acid groups, the sulfonic acid substituents are preferably in the 1-, 3- and 5- or 1,3- and 6-positions. When it is substituted by 2 acid groups the sulfonic acid substituents are preferably in the 1- and 3-, 1- and 5-, 3- and 5- or 3- and 6-positions. When it is substituted by one acid group the sulfonic acid substituent is preferably in the 1-, 3- or 5-position.

The invention also includes within its scope all the possible isomers, stereoisomers and their mixtures and the metabolites and the metabolic precursors or bio-precursors of the compounds as defined above.

As already said, the invention includes within its scope also the pharmaceutically acceptable salts of the ureido derivatives of formula (I).

Examples of pharmaceutically acceptable salts are either those with inorganic bases, such as sodium, potassium, calcium and aluminum hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines.

Sodium and potassium salts are preferred.

As stated above, the present invention also includes within its scope pharmaceutically acceptable bio-precursors (otherwise known as pro-drugs) of the compounds defined above, i.e. compounds which have a different formula from formula (I) above but which nevertheless upon administration to a human being are converted directly or indirectly in vivo into a ureido derivative of formula (I).

Preferred compounds are those wherein m and n in formula (I) are each 2 and each of the R groups is as defined above.

Examples of specific preferred compounds are:

7,7'-(carbonyl-bis(imino-N-methyl-4,2-pyrrolecargonylimino(N-methyl-4,2-pyrrole)carbonylimino))bis(3,5-naphthalendisulfonic acid);

7,7'-(carbonyl-bis(imino-N-methyl-4,2-pyrrolecargonylimino(N-methyl-4,2-pyrrole)carbonylimino))bis(3,6-naphthalendisulfonic acid);

7,7'-(carbonyl-bis(imino-N-methyl-4,2-pyrrolecargonylimino(N-methyl-4,2-pyrrole)carbonylimino))bis(1,3,5-naphthalentrisulfonic acid);

8,8'-(carbonyl-bis(imino-N-methyl-4,2-pyrrolecargonylimino(N-methyl-4,2-pyrrole)carbonylimino))bis(1,3,6-naphthalentrisulfonic acid);

7,7'-(carbonyl-bis(imino-N-methyl-4,2-pyrrolecargonylimino(N-methyl-4,2-pyrrole)carbonylimino))bis(1,3-naphthalendisulfonic acid);

7,7'-(carbonyl-bis(imino-N-methyl-4,2-pyrrolecargonylimino(N-methyl-4,2-pyrrole)carbonylimino))bis(2,4-naphthalendisulfonic acid);

8,8'-(carbonyl-bis(imino-N-methyl-4,2-pyrrolecargonylimino(N-methyl-4,2-pyrrole)carbonylimino))bis(2,4-naphthalendisulfonic acid);

8,8'-(carbonyl-bis(imino-N-methyl-4,2-pyrrolecargonylimino(N-methyl-4,2-pyrrole)carbonylimino))bis(1,3,5-naphthalentrisulfonic acid);

8,8'-(carbonyl-bis(imino-N-methyl-4,2-pyrrolecargonylimino(N-methyl-4,2-pyrrole)carbonylimino))bis(5-naphthalensulfonic acid);

8,8'-(carbonyl-bis(imino-N-methyl-4,2-pyrrolecargonylimino(N-methyl-4,2-pyrrole)carbonylimino))bis(1,3-naphthalendisulfonic acid);

8,8'-(carbonyl-bis(imino-N-methyl-4,2-pyrrolecargonylimino(N-methyl-4,2-pyrrole)carbonylimino))bis(3,5-naphthalendisulfonic acid);

8,8'-(carbonyl-bis(imino-N-methyl-4,2-pyrrolecargonylimino(N-methyl-4,2-pyrrole)carbonylimino))bis(1,5-naphthalendisulfonic acid);

8,8'-(carbonyl-bis(imino-N-methyl-4,2-pyrrolecargonylimino(N-methyl-4,2-pyrrole)carbonylimino))bis(3-naphthalensulfonic acid);

8,8'-(carbonyl-bis(imino-N-methyl-4,2-pyrrolecargonylimino(N-methyl-4,2-pyrrole)carbonylimino))bis(1-naphthalensulfonic acid);

2,2'-(carbonyl-bis(imino-N-methyl-4,2-pyrrolecargonylimino(N-methyl-4,2-pyrrole)carbonylimino))bis(1,5-naphthalendisulfonic acid);

7,7'-(carbonyl-bis(imino-N-methyl-4,2-pyrrolecargonylimino(N-methyl-4,2-pyrrole)carbonylimino))bis(1,6-naphthalendisulfonic acid);

7,7'-(carbonyl-bis(imino-N-methyl-4,2-pyrrolecargonylimino(N-methyl-4,2-pyrrole)carbonylimino))bis(2,6-naphthalendisulfonic acid);

7,7'-(carbonyl-bis(imino-N-methyl-4,2-pyrrolecargonylimino(N-methyl-4,2-pyrrole)carbonylimino))bis(1,5-naphthalendisulfonic acid);

7,7'-(carbonyl-bis(imino-N-methyl-4,2-pyrrolecargonylimino(N-methyl-4,2-pyrrole)carbonylimino))bis(2,5-naphthalendisulfonic acid);

7,7'-(carbonyl-bis(imino-N-methyl-4,2-pyrrolecargonylimino(N-methyl-4,2-pyrrole)carbonylimino))bis(2,3-naphthalendisulfonic acid);

8,8'-(carbonyl-bis(imino-N-methyl-4,2-pyrrolecargonylimino(N-methyl-4,2-pyrrole)carbonylimino))bis(1,6-naphthalendisulfonic acid);

8,8'-(carbonyl-bis(imino-N-methyl-4,2-pyrrolecargonylimino(N-methyl-4,2-pyrrole)carbonylimino))bis(2,6-naphthalendisulfonic acid);

8,8'-(carbonyl-bis(imino-N-methyl-4,2-pyrrolecargonylimino(N-methyl-4,2-pyrrole)carbonylimino))bis(2,5-naphthalendisulfonic acid);

8,8'-(carbonyl-bis(imino-N-methyl-4,2-pyrrolecargonylimino(N-methyl-4,2-pyrrole)carbonylimino))bis(3,6-naphthalendisulfonic acid);

8,8'-(carbonyl-bis(imino-N-methyl-4,2-pyrrolecargonylimino(N-methyl-4,2-pyrrole)carbonylimino))bis(2,3,5-naphthalentrisulfonic acid);

8,8'-(carbonyl-bis(imino-N-methyl-4,2-pyrrolecargonylimino(N-methyl-4,2-pyrrole)carbonylimino))bis(1,4,6-naphthalentrisulfonic acid);

8,8'-(carbonyl-bis(imino-N-methyl- 4,2-pyrrole)carbonylimino))bis(2,4,6-naphthalentrisulfonic acid);

7,7'-(carbonyl-bis(imino-N-methyl-4,2-pyrrolecargonylimino(N-methyl-4,2-pyrrole)carbonylimino))bis(1-naphthalensulfonic acid);

7,7'-(carbonyl-bis(imino-N-methyl-4,2-pyrrolecargonylimino(N-methyl-4,2-pyrrole)carbonylimino))bis(2-naphthalensulfonic acid);

7,7'-(carbonyl-bis(imino-N-methyl-4,2-pyrrolecargonylimino(N-methyl-4,2-pyrrole)carbonylimino))bis(3-naphthalensulfonic acid);

7,7'-(carbonyl-bis(imino-N-methyl-4,2-pyrrolecargonylimino(N-methyl-4,2-pyrrole)carbonylimino))bis(4-naphthalensulfonic acid);

7,7'-(carbonyl-bis(imino-N-methyl-4,2-pyrrolecargonylimino(N-methyl-4,2-pyrrole)carbonylimino))bis(1,4,6-naphthalentrisulfonic acid);

7,7'-(carbonyl-bis(imino-N-methyl-4,2-pyrrolecargonylimino(N-methyl-4,2-pyrrole)carbonylimino))bis(1,3,6-naphthalentrisulfonic acid);

7,7'-(carbonyl-bis(imino-N-methyl-4,2-pyrrolecargonylimino(N-methyl-4,2-pyrrole)carbonylimino) )bis(2,4,6-naphthalentrisulfonic acid);

7,7'-(carbonyl-bis(imino-N-methyl-4,2-pyrrolecargonylimino(N-methyl-4,2-pyrrole)carbonylimino))bis(2,3,5-naphthalentrisulfonic acid);

7,7'-(carbonyl-bis(imino-N-methyl-4,2-pyrrolecargonylimino))bis(1,3-naphthalenedisulfonic acid);

7,7'-(carbonyl-bis(imino-N-methyl-4,2-pyrrolecargonylimino(N-methyl-4,2-pyrrolecarbonylimino(N-methyl-4,2-pyrrole)carbonylimino))bis(1,3-naphthalenedisulfonic acid);

and the pharmaceutically acceptable salts thereof, in particular the sodium or potassium salt.

PHARMACOLOGY

The ureido derivatives of formula (I) and the pharmaceutically acceptable salts thereof, hereafter referred to as "the compounds of the invention" or "the active agents", have been found to be active in treating multiple sclerosis in mammals, including humans. Such therapeutic activity of the compounds of the invention is proven for instance by the fact that they have been found to be active in suppression of the development of experimental allergic encephalomyelitis (EAE) in rats and mice. As known, EAE is a demyelinating disease of the central nervous system used as experimental model of multiple sclerosis. According to the experimental frame-work female SJL mice (8–10 mice/group) were immunized with 200 $\mu$g of purified Myelin Basic Protein (MBP) emulsion in Freund Incomplete Adjuvant intradermally at the base of the tail. On the day of immunization and 48 hours later mice were injected intraperitoneally with 400 $\mu$g pertussis toxin. The representative compound of the invention PNU 153429 or saline were given intravenously to each group once a week for three consecutive times. Disease signs were evaluated daily from the onset, day 10–12, to day 21 according to the following clinical score scheme:

0—no clinical disease;
1—tail weakness;
2—paraparesis (incomplete paralysis of one or two hindlimbs);
3—paraplegia (complete paralysis of one or two hindlimbs);
4—paraplegia with forelimb weakness or paralysis;
5—moribund or dead animals.

Figure 1:
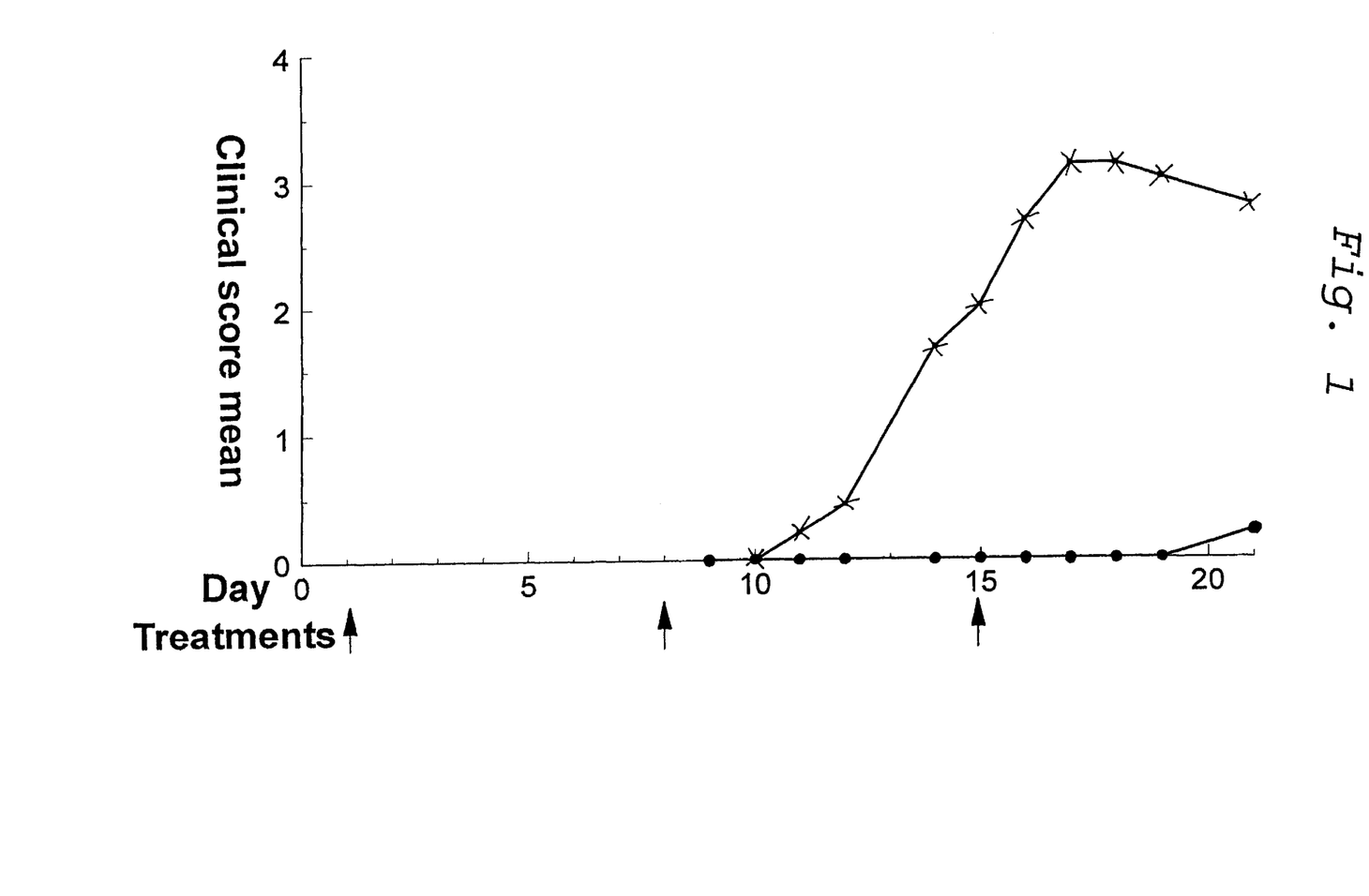

As can be seen from FIG. 1, PNU 153429 at the dose of 50 mg/kg completely prevented the development of EAE.

Figure 2:
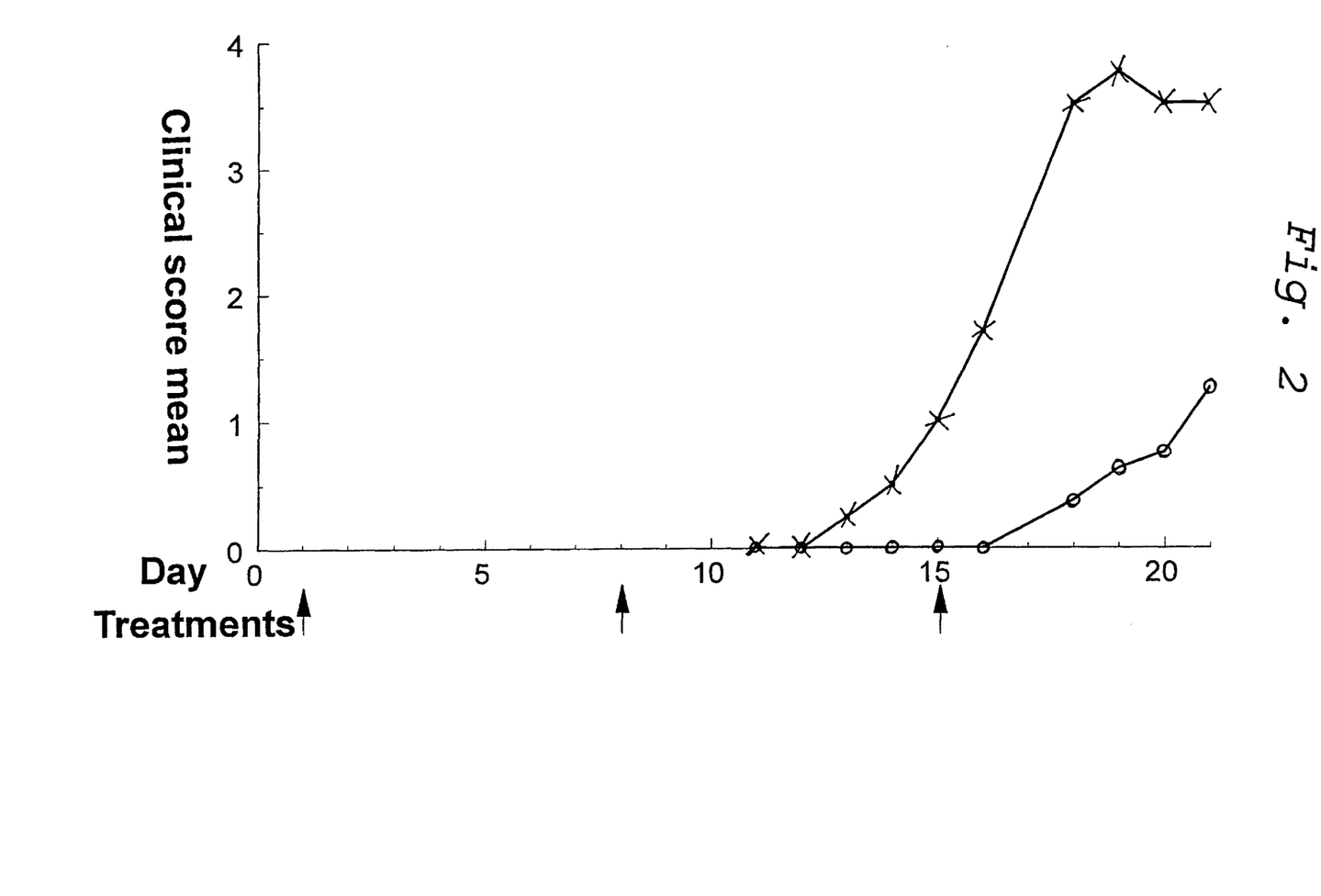

A significant reduction of the disease signs was obtained also by administering PNU 153429 at the dose of 25 mg/kg, as shown by FIG. 2.

LEGEND TO FIG. 1 AND 2

=PNU 153429 50 mg/kg i.v.
=PNU 153429 25 mg/kg i.v.
=Saline

The dosage of a compound of the invention to be administered to a patient suffering from multiple sclerosis will vary with the precise nature of the condition being treated and the recipient of the treatment.

A therapeutically effective dosage of the compounds of formula (I), for example the compound 2,2'-(carbonyl-bis (imino-N-methyl-4,2-pyrrolecarbonylimino(N-methyl-4,2-pyrrole)carbonylimino))bis(1,5-naphthalendisulfonic acid) tetrasodium salt, internal code PNU 153429 (FCE 27266) is in the range of 0.1–10 g per dose for adult humans. The suitable dosage can be administered in the form of a single dose or a series of doses separated by intervals of days, weeks or months.

The compounds of the invention can be therefore administered to patients suffering from relapsing-remitting, relapsing-progressive and chronic progressive multiple sclerosis.

The compounds of the invention will generally be administered to the patient in the form of a pharmaceutical formulation. Such formulations preferable include, in addition to the active agent, a physiologically acceptable carrier and/or diluent. Typical routes of administration are routinely parenteral, including intrathecal, transdermal, intravenous, intramuscular, subcutaneous and intraperitoneal injection, intravenous infusion or oral administration.

According to a preferred embodiment of the invention it is desirable to administer the active agents employed in the subject invention directly to the central nervous system. However, the existence of the blood-brain barrier limits the free passage of many types of molecules from the blood to cells of the central nervous system.

During the active phase of inflammatory diseases, such as multiple sclerosis, blood-brain lineage is known to occur and will permit entry of the compounds of the invention to the central nervous system. Nevertheless, there are several techniques that either physically break through the blood-brain barrier or circumvent it to deliver therapeutic agents. Examples of these techniques include intrathecal injections, surgical implants, and osmotic techniques.

A preferred embodiment for the administration of the compounds of the invention is by intrathecal injection, i.e., directly into the cerebrospinal fluid by puncturing the membranes surrounding the central nervous system. Puncturing of the membranes surrounding the central nervous system is usually by lumbar puncture. Sustained dosages of agents directly into the cerebrospinal fluid can be attained by the use of infusion pumps that are implanted surgically.

Another preferred embodiment for the administration of the compounds of the invention is by injection directly into the lumbar cerebrospinal fluid (intrathecally) or by injection intravenously.

Suitable carriers and diluents for liquid preparations include, but are not limited to, physiologically saline, glucose, buffered saline, olive oil, ethyl oleate, glycols, e.g. propylene glycol, and, if desired, a suitable amount of lidocaine hydrochloride.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

The compounds of the invention may be used in a method of treatment of multiple sclerosis comprising both separate and substantially contemporaneous administration of a composition containing a compound of formula (I), or a pharmaceutically acceptable salt thereof, and a pharmaceutical composition containing a further biologically active agent.

Object of the present invention is also to provide products containing a compound of the invention and a further biologically active agent as a combined preparation for simultaneous, separate or sequential use in treating multiple sclerosis.

The further biologically active agent can be either another compound of formula (I) or steroids, for example hydrocortisomers such as methylprednisolone, anti-inflammatory or anti-immune drugs, such as methotrexate, azathioprine, cyclophosphamide or cyclosporin A, or interferon-β, or antibodies, such as anti-CD4 antibodies, or mixtures thereof.

The compounds of the invention can be obtained according to PCT/EP91/00014, for instance by reacting a compound of formula (II)

wherein n and R are as defined above, or a salt thereof, with a compound of formula (III)

wherein each of the X groups, which may be the same or different, is a good leaving group, and if desired, salifying a compound of formula (I) thus obtained; and/or, if desired, obtaining a free compound of formula (I) from a salt thereof.

A salt of a compound of formula (II) may be a salt with in organic bases, for example those mentioned above as pharmaceutically acceptable salts used in the invention, the sodium and potassium salts being the preferred.

Preferred examples of leaving groups, according to the meaning of X, are halogen atoms, in particular chlorine, or other easily displaceable groups such as imidazolyl, triazolyl, p-nitrophenoxy, trichlorophenoxy or trichloromethyloxy. The reaction of a compound of formula (II), or a salt thereof, with a compound of formula (III) is an analogy process and can be carried out according to well known methods; for example according to the conditions described in organic chemistry for this kind of reaction, i.e. for synthesis of urea derivatives.

Preferably when in a compound of formula (III) X is a halogen atom, e.g. chlorine, the reaction may be carried out at a molar ratio of compound (II), or a salt thereof: compound (III) from about 1.1 to about 1.4. The reaction is preferably performed in organic solvents such as dimethylsulphoxide, hexamethylphosphotriamide, dimethyl-acetamide or, preferably, dimethylformamide, or their aqueous mixtures, or in water/dioxane or water/toluene mixtures, in the presence of either an organic base such as triethylamine or diisopropylethylamine, or an inorganic base such as sodium bicarbonate or sodium acetate. The reaction temperature may vary from about −10° C. to about 50° C. and the reaction time from about 1 to about 12 hours.

The compounds of the invention prepared according to the above described procedures may be purified by conventional methods such as by silica gel or alumina column chromatography, and/or by recrystallization from organic solvents such as lower aliphatic alcohols or dimethylformamide.

Analogously salification of a ureido derivative of formula (I) can be carried out by known methods in the art, as well as the conversion of a salt of a ureido derivative of formula (I) into a free product and the conversion of a ureido derivative of formula (I) into a pharmaceutically acceptable salt thereof.

The following examples further illustrate the present invention.

EXAMPLE 1

8,8'-(carbonyl-bis(imino-N-methyl-4,2-pyrrolecarbonylimino(N-methyl-4,2-pyrrole)carbonylimino))bis(3,5-naphthalendisulfonic acid) tetrasodium salt.

To a solution of 8-(amino-N-methyl-4,2-pyrrolecarbonylimino(N-methyl-4,2-pyrrole)carbonylimino))(3,5-naphthalendisulfonic acid) disodium salt hydrochloride (1256 mg, 2 mmols) in water (60 ml) and dioxane (20 ml), NaOH 1N (2 ml) and sodium acetate (328 mg, 4 mmols) was added under stirring.

The whole was cooled to 5° C. with an ice bath, then a solution of bis(trichloromethyl)carbonate (149 mg, 0.5 mmols) in dioxane (15 ml) was added dropwise in an hour. The mixture was stirred for 2 hours at room temperature. The solvents were evaporated under vacuum and the residue was chromatographed on a silica gel column with methylene chloride:methanol:water (300:200:20) as eluant, affording 856 mg of the title compound.

N.M.R. (DMSO-$d_6$): δ 3.85 (6H, s); 6.83 (1H, d, J=1.8); 7.06 (1H, d, J=1.8); 7.26 (1H, d, J=1.8); 7.38 (1H, d, J=1.08); 7.50 (1H, d, J=7.8) 7.72 (1H, dd, J=1.7, J=8.9); 7.98 (1H, d, J=7.8); 8, 25 (1H, bs); 9.19 (1H, d, J=1.7); 9.91 (1H, bs); 10.03 (1H, bs); U.V. ($H_2O$) nm: λ max ($E_{1\,cm}^{1\%}$): 310 (431); 231 (1027); F.A.B. M.S. m/z: 1209, $M^++H$; 640; 618; 614; 592.

By proceeding analogously, the following compounds can be prepared:

7,7'-(carbonyl-bis(imino-N-methyl-4,2-pyrrolecarbonylimino(N-methyl-4,2-pyrrole)carbonylimino))bis(3,5-naphthalendisulfonic acid) tetrasodium salt N.M.R. (DMSO-$d_6$): δ 3.85 (3H, S); 3.90 (3H, s); 6.81 (1H, d, J=1.8); 6.90 (1H, d, J=1.8); 7.12 (1H, d, J=1.8); 7.32 (1H, d, J=1.8); 7.70 (1H, dd, J=1.6, J=8.6); 7.80 (1H, d, J=8.6); 8.11 (1H, d, J=1.6); 8.15 (1H, bs), 8.58 (1H, d, J=1.7); 8.78 (1H, d, J=1.7); 10, 05 (1H, bs); 10.94 (1H, bs). F.A.B. M.S. m/z: 1209, $M^++H$; 1187, $M^+-Ne+H$; U.V. ($H_2O$) nm: λ max ($E_{1\,cm}^{1\%}$) 321 (416); 231 (721);

7,7'-(carbonyl-bis(imino-N-methyl-4,2-pyrrolecarbonylimino(N-methyl-4,2-pyrrole)carbonylimino))bis(3,6-naphthalendisulfonic acid) tetrasodium salt N.M.R. (DMSO-$d_6$): δ 3.85 (3H, s); 3.93 (3H, s); 6.81 (1H, d, J=1.8); 6.91 (1H, d, J=1.8); 7.08 (1H, d, J=1.8); 7.51 (1H, d, J=1.8); 7.68 (1H, dd, J=1.6, J=8.6); 7.78 (1H, d, J=8.6); 8.04 (1H, s); 8.12 (1H, bs); 8.23 (1H, s); 8.89 (1H, s); 10, 02 (1H, bs); 10, 98 (1H, bs); F.A.B. M.S. m/z: 1209, $M^++H$; 1187, $M^+-Ne+H$; U.V. ($H_2O$) nm: λ max ($E_{1\,cm}^{1\%}$): 323,4 (540); 227,7 (732)

7,7'-(carbonyl-bis(imino-N-methyl-4,2-pyrrolecarbonylimino(N-methyl-4,2-pyrrole)carbonylimino))bis(1,3,5-naphthalentrisulfonic acid) hexasodium salt N.M.R. (DMSO-$d_6$): δ 3.85 (3H, s); 3.89 (3H, s); 6.78 (1H, d, J=1.8); 7.08 (1H, d, J=1.8); 7.22 (1H, d, J=1.8); 7.35 (1H, d, J=1.8); 8.25 (1H, d, J=1.9); 8.30 (1H, bs); 8.36 (1H, bs); 9.00 (1H, bs); 9.07 (1H, d, J=1.6); 9.82 (1H, bs); 10, 20 (1H, bs); U.V. ($H_2O$) nm: λ max ($E_{1\,cm}^{1\%}$): 320 (374); 254 (444)

8,8'-(carbonyl-bis(imino-N-methyl-4,2-pyrrolecarbonylimino(N-methyl-4,2-pyrrole)carbonylimino))bis(1,3,6-naphthalen-trisulfonic acid); hexasodium salt N.M.R. (DMSO-$d_6$): δ 3.84 (3H, S); 3.88 (3H, s); 6.81 (1H, d, J=1.8); 7.07 (1H, d, J=1.8); 7.11 (1H, d, J=1.8); 7.42 (1H, d, J=1.8); 7.87 (1H, d, J=1.9); 7.87 (1H, d, J=1.9); 8.06 (1H, d, J=1.9); 8.12 (1H, bs); 8, 33 (1H, d, J=1.9); 8, 54 (1H, d, J=1.9); 9.93 (1H, bs); 12.19 (1H, bs); U.V. ($H_2O$) nm: λ max ($E_{1\,cm}^{1\%}$) 320 (374); 254 (444)

7,7'-(carbonyl-bis(imino-N-methyl-4,2-pyrrolecarbonylimino(N-methyl-4,2-pyrrole)carbonylimino))bis(1,3-naphthalendisulfonic acid) tetrapotassium salt I.R. (KBr) $cm^{-1}$: 3450 (b); 1650; 1580; 1530; 1190; 1030; N.M.R. (DMSO-$d_6$): δ 3.84 (3H, s); 3.87 (3H, s); 6.80 (1H, d); 7.05 (1H, d); 7.18 (1H, d); 7.33 (1H, d); 7.86 (2H, m);8.00 (1H, d,); 8.16 (1H, bs); 8.21 (1H, d); 8, 95 (1H, bs); 9, 86 (1H, bs); 10.21 (1H, bs); F.A.B. M.J. m/z: 1273 ($M^++H$); 1311 (($M^++K$); U.V. ($H_2O$) nm: λ max ($E_{1\,cm}^{1\%}$): 316.8 (371); 248.95 (444)

7,7'-(carbonyl-bis(imino-N-methyl-4,2-pyrrolecarbonylimino(N-methyl-4,2-pyrrole)carbonylimino))bis(2,4-naphthalendisulfonic acid) tetrasodium salt N.M.R. (DMSO-$d_6$): δ 3.85 (3H, s); 3.89 (3H, s); 6.81 (1H, d, J=1.7); 7.06 (1H, d, J=1.7); 7.22 (1H, d, J=1.7); 7.33 (1H, d, J=1.7); 7.33 (1H, d, J=1.7); 7.38 (1H, dd, J=2.0, J=9.5); 7.92 (1H, bs); 8.10 (1H, d, J=1.7); 8.20 (1H, bs); 8, 32 (1H, d, J=2.0); 8, 69 (1H, d, J=9.4); 9.88 (1H, bs); 10.08 (1H, bs);

8,8'-(carbonyl-bis(imino-N-methyl-4,2-pyrrolecarbonylimino(N-methyl-4,2-pyrrole)carbonylimino))bis(2,4-naphthalendisulfonic acid) tetrasodium salt N.M.R. (DMSO-$d_6$): δ 3.85 (6H, s); 6.81 (1H, d, J=1.7 Hz) 7.06 (1H, d, J=1+Hz); 7.25 (1H, d, J=1.7 Hz); 7.34 (1H, d, J=1.7 Hz); 7.4, 7.6 (2H, m); 8.14 (1H, bs);8.25 (2H, s,); 8.73 (1H, dd, J=13 Hz, J=8, 3 Hz); 9.92 (1H, bs); 10.07 (1H, bs); U.V. ($H_2O$) nm: λ max ($E_{1\,cm}^{1\%}$) 307 (435); 231 (932); F.A.B. m/z: 1209 ($M^++1$); 1231 ($M^++Ne$); 1128 ($M^+-SO_3$)

8,8'-(carbonyl-bis(imino-N-methyl-4,2-pyrrolecarbonylimino(N-methyl-4,2-pyrrole)carbonylimino))bis(1,3,5-naphthalen-trisulfonic acid) hexasodium salt I.R. (KBr) $cm^{-1}$: 3440 b, 1640, 1590, 1190, 1030; N.M.R. (DMSO-$d_6$): δ 3.80 (3H, S); 3.83 (3H, s); 6.80 (1H, d); 7.06 (2H, m); 7.40 (1H, d); 7.88 (1H, d); 7.99 (1H, d);8.02 (1H, bs); 8.57 (1H, d); 9.33 (1H, d); 9.91 (1H, bs); 12.29 (1H, bs); U.V. ($H_2$) nm: λ max ($E_{1\,cm}^{1\%}$): 311 (266); 233 (551); F.A.B.–M.S. m/z 1411, $M^--H$;1389, $M^--Na$ 8,8'-(carbonyl-bis(imino-N-methyl-4,2-pyrrolecarbonylimino(N-methyl-4,2-pyrrole)carbonylimino))bis(5-naphthalensulfonic acid) disodium salt N.M.R. (DMSO-$d_6$): δ 3.85 (6H, s); 6.84 (1H, d, J=1.8); 7.05 (1H, d, J=1.8); 7.25 (1H, d, J=1.8); 7.35 (1H, d, J=1.8); 7.46–7.56 (3H, m); 7.92–8.00 (2H, m); 8.15 (1H, bs); 8, 87 (1H, m); 9,89 (1H, bs); 10.03 (1H, bs); U.V. ($H_2O$) nm: λ max ($E_{1\,cm}^{1\%}$) 310 (531); 227 (1043); F.A.B. M.S. m/z: 1005, ($M^++H$); 1027 ($M^++Ne$); 512

8,8'-(carbonyl-bis(imino-N-methyl-4,2-pyrrolecarbonylimino(N-methyl-4,2-pyrrole)carbonylimino))bis(1,3-naphthalendisulfonic acid) tetrasodium salt N.M.R. (DMSO-d$_6$): δ 3.84 (3H, s); 3.86 (3H, s); 6.81 (1H, d, J=1.8); 7.08 (2H, bs); 7.41 1H, d, J=1.8); 7.50 (1H, t, J=7.0); 7.78 (1H, d, J=7.0); 8.02 (1H, d, J=7.0); 8.11 (2H, m); 8.53 (1H, d, J=2.02); 9.93 (1H, bs); 12.21 (1H, bs); U.V. (H$_2$O) nm: λ max (E$_{1\ cm}^{1\%}$): 309.05 (403); 229,65 (735); F.A.B. M.S. m/z: 1209, M$^+$+H; 1231, M$^+$+Ne; 1187, M$^+$−Ne+H; 1129; 640; 618; 614; 592

2,2'-(carbonyl-bis(imino-N-methyl-4,2-pyrrolecarbonylimino(N-methyl-4,2-pyrrole)carbonylimino))bis(1,5-naphthalendisulfonic acid) tetrasodium salt N.M.R. (DM d 0-d$_6$): 3.85 (3H, s); 3.91 (3H, s); 6.90 (1H, d, J=1.8); 6.98 (1H, d, J=1.8); 7.09 (1H, d, J=1.8); 7.35 (1H, dd, J=7, J=8.8); 7.47 (1H, d, J=1.8); 7.9 (1H, d, J=7); 9.15 (1H, bs); 8.67–8.82 (2H, dd, J=9.6); 8.99 (1H, d, J=8.8); 9.98 (1H, bs); 12.64 (1H, bs); F.A.B. M.S.: m/z 1207, [M−H]$^-$; 1185, [M−23]$^-$; 1105 (M−SO$_3$Na)$^-$; U.V. (H$_2$O): nm: λ max 298; (E$_{1\ cm}^{1\%}$) 522

8,8'-(carbonyl-bis(imino-N-methyl-4,2-pyrrolecarbonylimino(N-methyl-4,2-pyrrole)carbonylimino))bis(1,5-naphthalendisulfonic acid) tetrasodium salt I.R. (KBr) cm$^{-1}$: 3440 b, 1660, 1640, 1585, 1180, 1030; N.M.R. (DMSO-d$_6$): δ 3.84 (3H, s); 3.85 (3H, s); 6.80 1H, d); 7.07 (2H, m); 7.41 2H, m); 7.92 (2H, dd); 8.12 (1.12 (1H, s); 8, 27 (1H, dd); 9.07 (1H, dd); 9.90 (1H, bs); 12.27 (1H, bs); U.V. (H$_2$O) nm: λ max (E$_{1\ cm}^{1\%}$): 316 (331); 229 (478); F.A.B. −M.S. m/z: 1209, M$^+$+1; 1231, M$^+$+23; 1128, M−80

8,8'-(carbonyl-bis(imino-N-methyl-4,2-pyrrolecarbonylimino(N-methyl-4,2-pyrrole)carbonylimino))bis(3-naphthalensulfonic acid) disodium salt I.R. (KBr)cm$^{-1}$: 3430 b, 1640, 1585, 1200, 1030; N.M.R. (DMSO-d$_6$): δ 3.84 (6H, s); 6.86 (1H, d); 7.05 (1H, d); 7.24 (1H, d); 7.35 (1H, d) 7.54 (2H, m); 7.70 (1H, dd); 7.90 (2H, m); 8.15 (1H, d); 8.15 (1H, d); 8.95 (1H, bs); 9.94 (1H, bs); 10.03 (1H, bs); U.V. (H$_2$O) nm: λ max (E$_{1\ cm}^{1\%}$) 304 (366); 226 (1002) F.A.B. M.S.:m/z 1005, M$^+$+H; 1027, M$^+$+2Na 8,8'-(carbonyl-bis(imino-N-methyl-4,2-pyrrolecarbonylimino(N-methyl-4,2-pyrrole)carbonylimino))bis(1-naphthalensulfonic acid) disodium salt N.M.R. (DMSO-d$_6$): δ 3.84 (3H, s); 3.85 (3H, s); 6.82 (1H, d, J=1.8); 7.06 (1H, d, J=1.8); 7.09 (1H, d, J=1.8); 7.39–7.54 (3H, m); 7.74 (1H, dd, J=1.3, J=0.3, J=8.2); 7.93–8.02 (2H, m); 8.13 (1H, bs); 8.26 (1H, dd, J=1.5, J=7.3); 9.93 (1H, bs); 12.20 (1H, bs); F.A.B. M.S.: m/z 1005, M$^+$+H; 1027, M$^+$+Ne; U.V. (H$_2$O) nm: λ max (E$_{1\ cm}^{1\%}$): 312 (490); 224 (831)

7,7'-(carbonyl-bis(imino-N-methyl-4,2-pyrrolecarbonylimino(N-methyl-4,2-pyrrole)carbonylimino))bis(1,6-naphthalendisulfonic acid) tetrasodium salt;

7,7'-(carbonyl-bis(imino-N-methyl-4,2-pyrrolecarbonylimino(N-methyl-4,2-pyrrole)carbonylimino))bis(2,6-naphthalendisulfonic acid) tetrasodium salt;

7,7'-(carbonyl-bis(imino-N-methyl-4,2-pyrrolecarbonylimino(N-methyl-4,2-pyrrole)carbonylimino))bis(1,5-naphthalendisulfonic acid) tetrasodium salt;

7,7'-(carbonyl-bis(imino-N-methyl-4,2-pyrrolecarbonylimino(N-methyl-4,2-pyrrole)carbonylimino))bis(2,5-naphthalendisulfonic acid) tetrasodium salt;

7,7'-(carbonyl-bis(imino-N-methyl-4,2-pyrrolecarbonylimino(N-methyl-4,2-pyrrole)carbonylimino))bis(2,3-naphthalendisulfonic acid) tetrasodium salt;

8,8'-(carbonyl-bis(imino-N-methyl-4,2-pyrrolecarbonylimino(N-methyl-4,2-pyrrole)carbonylimino))bis(1,6-naphthalendisulfonic acid) tetrasodium salt;

8,8'-(carbonyl-bis(imino-N-methyl-4,2-pyrrolecarbonylimino(N-methyl-4,2-pyrrole)carbonylimino))bis(2,6-naphthalendisulfonic acid) tetrasodium salt;

8,8'-(carbonyl-bis(imino-N-methyl-4,2-pyrrolecarbonylimino(N-methyl-4,2-pyrrole)carbonylimino))bis(2,5-naphthalendisulfonic acid) tetrasodium salt;

8,8'-(carbonyl-bis(imino-N-methyl-4,2-pyrrolecarbonylimino(N-methyl-4,2-pyrrole)carbonylimino))bis(3,6-naphthalendisulfonic acid) tetrasodium salt;

8,8'-(carbonyl-bis(imino-N-methyl-4,2-pyrrolecarbonylimino(N-methyl-4,2-pyrrole)carbonylimino))bis(2,3,5-naphthalentrisulfonic acid) hexasodium salt;

8,8'-(carbonyl-bis(imino-N-methyl-4,2-pyrrolecarbonylimino(N-methyl-4,2-pyrrole)carbonylimino))bis(1,4,6-naphthalentrisulfonic acid) hexasodium salt;

8,8'-(carbonyl-bis(imino-N-methyl-4,2-pyrrolecarbonylimino(N-methyl-4,2-pyrrole)carbonylimino))bis(2,4,6-naphthalentrisulfonic acid) hexasodium salt;

7,7'-(carbonyl-bis(imino-N-methyl-4,2-pyrrolecarbonylimino(N-methyl-4,2-pyrrole)carbonylimino))bis(1-naphthalensulfonic acid)disodium salt;

7,7'-(carbonyl-bis(imino-N-methyl-4,2-pyrrolecarbonylimino(N-methyl- 4,2-pyrrole)carbonylimino))bis(2-naphthalensulfonic acid)disodium salt;

7,7'-(carbonyl-bis(imino-N-methyl-4,2-pyrrolecarbonylimino(N-methyl-4,2-pyrrole)carbonylimino))bis(3-naphthalensulfonic acid)disodium salt;

7,7'-(carbonyl-bis(imino-N-methyl-4,2-pyrrolecarbonylimino(N-methyl-4,2-pyrrole)carbonylimino))bis(4-naphthalensulfonic acid)disodium salt;

7,7'-(carbonyl-bis(imino-N-methyl-4,2-pyrrolecarbonylimino(N-methyl-4,2-pyrrole)carbonylimino))bis(1,4,6-naphthalentrisulfonic acid) hexasodium salt;

7,7'-(carbonyl-bis(imino-N-methyl-4,2-pyrrolecarbonylimino(N-methyl-4,2-pyrrole)carbonylimino))bis(1,3,6-naphthalentrisulfonic acid) hexasodium salt;

7,7'-(carbonyl-bis(imino-N-methyl-4,2-pyrrolecarbonylimino(N-methyl-4,2-pyrrole)carbonylimino))bis(2,4,6-naphthalentrisulfonic acid) hexasodium salt; and 7,7'-(carbonyl-bis(imino-N-methyl-4,2-pyrrolecarbonylimino(N-methyl-4,2-pyrrole)carbonylimino))bis(2,3,5-naphthalentrisulfonic acid) hexasodium salt.

EXAMPLE 2

8,8'-(carbonyl-bis(imino-N-methyl-4,2-pyrrolecarbonylimino(N-methyl-4,2-pyrrole)carbonylimino))-bis(3,5-naphthalenedisulfonic acid)

A solution of 8,8'-(carbonyl-bis(imino-N-methyl-4,2-pyrrolecarbonylimino(N-methyl-4,2-pyrrole)

carbonylimino))-bis (3,5-naphthalenedisulfonic acid) tetrasodium salt (400 mg) in water (10 ml), is chromatographed on an Amberlite 1R-120(H) column (20 ml), with water as eluent.

The solution is evaporated to dryness in vacuum, affording 0.3 g of the title compound.

By proceeding analogously the following compounds can be obtained:

7,7'-(carbonyl-bis(imino-N-methyl-4,2-pyrrolecarbonylimino)) bis(1,3-naphthalenedisulfonic acid) tetrapotassium salt $^1$H-NMR (200 MHz, DMSO): δ 3.86 (s, 3H); 6.98, 7.15 (two-d, J=1.9 Hz, 2H); 7.87 (m, 2H); 8.00 (d, J=1.7 Hz, 1H); 8.17 (s, 1H); 8.22 (d, J=1.7 Hz, 1H); 8.90 (s, 1H); 10.08 (s, 1H);

7,7'-(carbonyl-bis(imino-N-methyl-4,2-pyrrolecarbonylimino(N-methyl-4,2-pyrrolecarbonylimino(N-methyl-4,2-pyrrole)carbonylimino))bis(1,3,-naphthalenedisulfonic acid), tetrapotassium salt;

$^1$H-NMR (200 MHz, DMSO): δ 3.84, 3.86, 3.88 (three-s, 9H); 6.80, (d, J=1.7 Hz, 1H); 7.05 (m, 2H); 7.20 (d, J=1.6 Hz, 1H); 7.25 (d, J=1.6 Hz, 1H); 7.34 (d, J=1.6 Hz, 1H); 7.87 (m, 2H); 7.80 (d, J=1.7 Hz, 1H); 8.16 (s, 1H); 8.21 (d, J=1.7 Hz, 1H); 8.95 (s, 1H); 9.85, 9.99, 10.23 (three-s, 3H).

EXAMPLE 3

Intramuscular injection 40 mg/ml

An injectable pharmaceutical preparation can be manufactured by dissolving 40 g of 2,2'-(carbonyl-bis(imino-N-methyl-4,2-pyrrolecarbonylimino(N-methyl-4,2-pyrrole)carbonylimino))-bis (1,5-naphthalenedisulfonic acid) tetrasodium salt in water for injection (1000 ml) and sealing ampoules of 1–10 ml.

We claim:

1. A method of treating a patient suffering from multiple sclerosis, comprising administering an effective amkount of uriedo derivitive of formula (I):

wherein
each of m and n, which arehe same, is an integer of 1 to 3; and
each of the groups, which are the same, is a naphthyl group substituted by 1 to 3 sulfonic acid groups,
or a pharmacuetically acceptable salt thereof.

2. The method of claim 1, wherein m and n are each 2.

3. The method of claim 1, wherein a sodium or a potassium salt of the ureido derivative of formula I is administered to the patient.

4. A method of treating a patient suffering from multiple sclerosis, comprising administering to the patient, either separately or substantially simultaneously, a ureido derivative of formula (I):

wherein
each of m and n, which are the same, is an integer of 1 to 3; and
each of the R groups, which are the same, is a naphthyl group substituted by 1 to 3 sulfonic acid groups,
or a pharmaceutically acceptable salt thereof; and
a second biologically active agent selected from the group consisting of another ureido derivative of formula (I), a steroid, an anti-inflammatory agent, an anti-immune agent, interferon-β, an antibody, and mixtures thereof.

5. The method of claim 4, wherein m and n are each 2.

6. The method of claim 4, wherein a sodium or a potassium salt of the ureido derivative of formula (I) is administered to the patient.

7. The method of claim 4, wherein the second biologically active agent is another ureido derivative of formula (I).

8. A method of treating a patient suffering from multiple sclerosis, which method comprises administering to the patient an effective amount of the compound 2,2'-(carbonyl-bis (imino-N-methyl-4,2-pyrrolecarbonylimino(N-methyl-4,2-pyrrole)carbonylimino))bis(1,5-naphthalendisulfonic acid) tetrasodium salt, or a pharmaceutically acceptable salt thereof.

9. A method of treating a patient suffering from multiple sclerosis, which method comprises administering to the patient an effective amount of a compound selected from:

7,7'-(carbonyl-bis(imino-N-methyl-4,2-pyrrolecarbonylimino (N-methyl-4,2-pyrrole) carbonylimino))bis(3,5-naphthalendisulfonic acid);

7,7'-(carbonyl-bis(imino-N-methyl-4,2-pyrrolecarbonylimino (N-methyl-4,2-pyrrole) carbonylimino))bis(3,6-naphthalendisulfonic acid);

7,7'-(carbonyl-bis(imino-N-methyl-4,2-pyrrolecarbonylimino (N-methyl-4,2-pyrrole) carbonylimino))bis(1,3,5-naphthalentrisulfonic acid);

8,8'-(carbonyl-bis(imino-N-methyl-4,2-pyrrolecarbonylimino(N-methyl-4,2-pyrrole) carbonylimino))bis (1,3,6-naphthalen-trisulfonic acid);

7,7'-(carbonyl-bis(imino-N-methyl-4,2-pyrrolecarbonylimino (N-methyl-4,2-pyrrole) carbonylimino))bis(1,3-naphthalendisulfonic acid);

7,7'-(carbonyl-bis(imino-N-methyl-4,2-pyrrolecarbonylimino (N-methyl-4,2-pyrrole) carbonylimino))bis(2,4-naphthalendisulfonic acid);

8,8'-(carbonyl-bis(imino-N-methyl-4,2-pyrrolecarbonylimino (N-methyl-4,2-pyrrole) carbonylimino))bis(2,4-naphthalendisulfonic acid);

8,8'-(carbonyl-bis(imino-N-methyl-4,2-pyrrolecarbonylimino (N-methyl-4,2-pyrrole) carbonylimino))bis(1,3,5-naphthalentrisulfonic acid);

8,8'-(carbonyl-bis(imino-N-methyl-4,2-pyrrolecarbonylimino (N-methyl-4,2-pyrrole)carbonylimino))bis(5-naphthalen-sulfonic acid);

8,8'-(carbonyl-bis(imino-N-methyl-4,2-pyrrolecarbonylimino (N-methyl-4,2-pyrrole)carbonylimino))bis(1,3-naphthalendisulfonic acid);

8,8'-(carbonyl-bis(imino-N-methyl-4,2-pyrrolecarbonylimino (N-methyl-4,2-pyrrole)carbonylimino))bis(3,5-naphthalendisulfonic acid);

8,8'-(carbonyl-bis(imino-N-methyl-4,2-pyrrolecarbonylimino (N-methyl-4,2-pyrrole)carbonylimino))bis(1,5-naphthalendisulfonic acid);

8,8'-(carbonyl-bis(imino-N-methyl-4,2-pyrrolecarbonylimino (N-methyl-4,2-pyrrole)carbonylimino))bis(3-naphthalensulfonic acid);

8,8'-(carbonyl-bis(imino-N-methyl-4,2-pyrrolecarbonylimino (N-methyl-4,2-pyrrole)carbonylimino))bis(1-naphthalensulfonic acid);

7,7'-(carbonyl-bis(imino-N-methyl-4,2-pyrrolecarbonylimino (N-methyl-4,2-pyrrole)carbonylimino))bis(1,6-naphthalendisulfonic acid);

7,7'-(carbonyl-bis(imino-N-methyl-4,2-pyrrolecarbonylimino (N-methyl-4,2-pyrrole)carbonylimino))bis(2,6-naphthalendisulfonic acid);

7,7'-(carbonyl-bis(imino-N-methyl-4,2-pyrrolecarbonylimino (N-methyl-4,2-pyrrole)carbonylimino))bis(1,5-naphthalendisulfonic acid);

7,7'-(carbonyl-bis(imino-N-methyl-4,2-pyrrolecarbonylimino (N-methyl-4,2-pyrrole)carbonylimino))bis(2,5-naphthalendisulfonic acid);

7,7'-(carbonyl-bis(imino-N-methyl-4,2-pyrrolecarbonylimino (N-methyl-4,2-pyrrole)carbonylimino))bis(2,3-naphthalendisulfonic acid);

8,8'-(carbonyl-bis(imino-N-methyl-4,2-pyrrolecarbonylimino (N-methyl-4,2-pyrrole)carbonylimino))bis(1,6-naphthalendisulfonic acid);

8,8'-(carbonyl-bis(imino-N-methyl-4,2-pyrrolecarbonylimino (N-methyl-4,2-pyrrole)carbonylimino))bis(2,6-naphthalendisulfonic acid);

8,8'-(carbonyl-bis(imino-N-methyl-4,2-pyrrolecarbonylimino (N-methyl-4,2-pyrrole)carbonylimino))bis(2,5-naphthalendisulfonic acid);

8,8'-(carbonyl-bis(imino-N-methyl-4,2-pyrrolecarbonylimino (N-methyl-4,2-pyrrole)carbonylimino))bis(3,6-naphthalendisulfonic acid);

8,8'-(carbonyl-bis(imino-N-methyl-4,2-pyrrolecarbonylimino (N-methyl-4,2-pyrrole)carbonylimino))bis(2,3,5-naphthalentrisulfonic acid);

8,8'-(carbonyl-bis(imino-N-methyl-4,2-pyrrolecarbonylimino (N-methyl-4,2-pyrrole)carbonylimino))bis(1,4,6-naphthalentrisulfonic acid);

8,8'-(carbonyl-bis(imino-N-methyl-4,2-pyrrolecarbonylimino (N-methyl-4,2-pyrrole)carbonylimino))bis(2,4,6-naphthalentrisulfonic acid);

7,7'-(carbonyl-bis(imino-N-methyl-4,2-pyrrolecarbonylimino (N-methyl-4,2-pyrrole)carbonylimino))bis(1-naphthalensulfonic acid);

7,7'-(carbonyl-bis(imino-N-methyl-4,2-pyrrolecarbonylimino (N-methyl-4,2-pyrrole)carbonylimino))bis(2-naphthalensulfonic acid);

7,7'-(carbonyl-bis(imino-N-methyl-4,2-pyrrolecarbonylimino (N-methyl-4,2-pyrrole)carbonylimino))bis(3-naphthalensulfonic acid);

7,7'-(carbonyl-bis(imino-N-methyl-4,2-pyrrolecarbonylimino (N-methyl-4,2-pyrrole)carbonylimino))bis(4-naphthalensulfonic acid);

7,7'-(carbonyl-bis(imino-N-methyl-4,2-pyrrolecarbonylimino (N-methyl-4,2-pyrrole)carbonylimino))bis(1,4,6-naphthalentrisulfonic acid);

7,7'-(carbonyl-bis(imino-N-methyl-4,2-pyrrolecarbonylimino (N-methyl-4,2-pyrrole)carbonylimino))bis(1,3,6-naphthalentrisulfonic acid);

7,7'-(carbonyl-bis(imino-N-methyl-4,2-pyrrolecarbonylimino))bis (1,3-naphthalenedisulfonic acid);

7,7'-(carbonyl-bis(imino-N-methyl-4,2-pyrrolecarbonylimino(N-methyl-4,2-pyrrolecarbonylimino(N-methyl-4,2-pyrrole)carbonylimino))bis(1,3-naphthalenedisulfonic acid);

7,7'-(carbonyl-bis(imino-N-methyl-4,2-pyrrolecarbonylimino (N-methyl-4,2-pyrrole)carbonylimino))bis(2,4,6-naphthalentrisulfonic acid);

7,7'-(carbonyl-bis(imino-N-methyl-4,2-pyrrolecarbonylimino (N-methyl-4,2-pyrrole)carbonylimino))bis(2,3,5-naphthalentrisulfonic acid); or a pharmaceutically acceptable salt thereof.

* * * * *

UNITED STATES PATENT AND TRADEMARK OFFICE
CERTIFICATE OF CORRECTION

PATENT NO. : 5,859,046
DATED : January 12, 1999
INVENTOR(S) : Rachele ALZANI et al.

It is certified that error appears in the above-identified patent and that said Letters Patent is hereby corrected as shown below:

On the title page, item [54], Col.1, in the title should read:

--BIOLOGICALLY ACTIVE UREIDO DERIVATIVES USEFUL IN THE TREATMENT OF MULTIPLE SCLEROSIS--

Signed and Sealed this

Thirteenth Day of July, 1999

Attest:

Q. TODD DICKINSON

*Attesting Officer*   *Acting Commissioner of Patents and Trademarks*